United States Patent [19]

Brown et al.

[11] 4,276,296

[45] Jun. 30, 1981

[54] SUBSTITUTED BENZOPYRANO[3,4-C]PYRIDINES, COMPOSITIONS AND USE THEREOF

[75] Inventors: Richard E. Brown, Hanover; Chester Puchalski, Dover; John Shavel, Jr., Mendham, all of N.J.

[73] Assignee: Warner-Lambert Company, Morris Plains, N.J.

[21] Appl. No.: 97,014

[22] Filed: Nov. 23, 1979

Related U.S. Application Data

[63] Continuation-in-part of Ser. No. 916,397, Jun. 16, 1978, abandoned, which is a continuation-in-part of Ser. No. 743,839, Nov. 11, 1976, abandoned, which is a continuation-in-part of Ser. No. 548,298, Feb. 10, 1975, abandoned.

[51] Int. Cl.$^3$ .................. A61K 31/44; A61K 31/445; C07D 491/052
[52] U.S. Cl. .................. 424/256; 424/267; 546/92
[58] Field of Search .................. 546/92; 424/256, 267

[56] References Cited

U.S. PATENT DOCUMENTS

| 3,946,008 | 3/1974 | Brown et al. ...... 546/92 |
| 3,961,057 | 6/1976 | Brown et al. ...... 546/92 |

OTHER PUBLICATIONS

Austen et al., *Asthma*, (1973), Academic Press, pp. 29-38, 92-107, 169-184.

*Primary Examiner*—Henry R. Jiles
*Assistant Examiner*—R. W. Ramsuer
*Attorney, Agent, or Firm*—Walter Patton

[57] ABSTRACT

Substituted benzopyrano[3,4-c]pyridines and processes for their preparation are disclosed. The compounds are active as bronchodilators.

8 Claims, No Drawings

SUBSTITUTED BENZOPYRANO[3,4-C]PYRIDINES, COMPOSITIONS AND USE THEREOF

CROSS REFERENCES TO RELATED APPLICATIONS

This is a continuation-in-part application of copending U.S. Ser. No. 916,397, filed June 16, 1978, now abandoned, which is a continuation-in-part application of copending U.S. Ser. No. 743,839, filed Nov. 11, 1976, now abandoned, which is a continuation-in-part application of copending U.S. Ser. No. 548,298, filed Feb. 10, 1975, now abandoned.

SUMMARY OF THE INVENTION

This invention relates to novel substituted benzopyrano[3,4-c]pyridines having the formula:

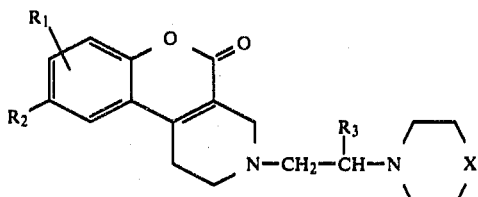

(I)

wherein $R_1$ and $R_2$ are lower alkoxy of 1-6 carbon atoms; $R_3$ is lower alkyl of 1-6 carbon atoms and X is $CH_2$ or a bond connecting the adjacent carbon atoms and pharmaceutically acceptable salts thereof.

The preferred compounds of the present invention are those wherein $R_1$ and $R_2$ are methoxy. Still further preferred compounds are designated 1,2,3,4-tetrahydro-8,9-dimethoxy-3-[2-methyl-2-(1-piperidinyl)ethyl]-5-[1]benzopyrano[3,4-c]-pyridin-5-one; and 1,2,3,4-tetrahydro-8,9-dimethoxy-3-[2-methyl-2-(1-pyrrolidinyl)ethyl]-5H-[1]benzopyrano[3,4-c]pyridin-5-one and the maleate salts thereof.

The compounds of formula I have an asymmetrical center at the carbon atom to which $R_3$ is attached and consequently the compounds exist in both D- and L-optical isomeric forms. It is to be understood that formula I as used throughout the description of this invention encompasses both the D- and L-optical isomers.

The novel substituted benzopyrano[3,4-c]pyridines of the invention can be prepared by the following reaction sequence wherein $R_1$, $R_2$, $R_3$ and X are as defined above.

In the sequence, an alpha-halocarbonyl compound of formula III is reacted with a compound having the formula II to afford an alkylated intermediate of formula IV. In formula III, Hal-refers to halogen such as chlorine or bromine.

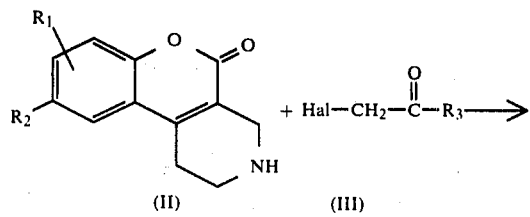

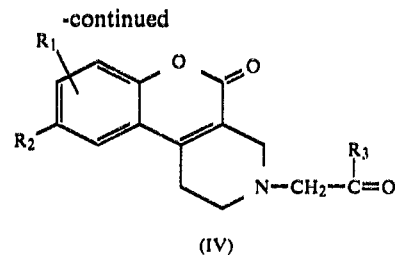

(IV)

The compounds of the invention having formula I can be prepared from the alkylated intermediates of formula IV by a reductive alkylation reaction according to the following equation:

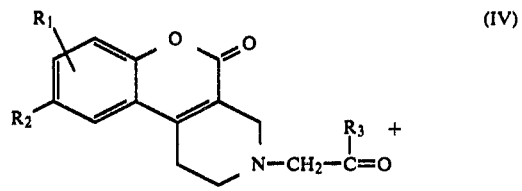

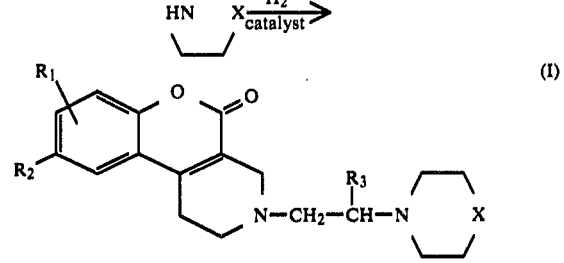

The catalyst used in the reductive alkylation may be a noble metal catalyst such as palladium, platinum, or rhodium, or may be a catalyst such as Raney nickel or Raney cobalt. The reaction is preferably carried out in a solvent such as methanol, ethanol or ethyl acetate.

The compounds of formula II can be prepared by reacting a substituted phenol of the formula:

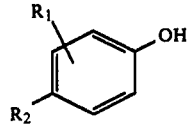

with 3-carbethoxy-4-piperidone of the formula:

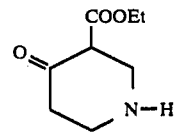

in the presence of an acid catalyst. Examples of the acid catalysts which can be employed in this reaction are sulfuric acid, phosphoric acid, phosphorous oxychloride, phosphorous pentoxide, polyphosphoric acid, boronfluoride and the like. The starting phenolic compounds, which may be, for example, 3,4-dimethoxyphenol; 2,4-dimethoxyphenol, or 4,5-dimethoxyphenol, are known compounds. The alpha-halocarbonyl compounds of formula III and the amines of structure V are known compounds and are either commercially available or may be prepared according to methods known in the art.

The pharmaceutically acceptable acid addition salts of the compounds of formula I may be prepared by conventional reactions with equivalent amounts or slight excess of organic or inorganic acids. Examples of pharmaceutically acceptable salts are the the salts of maleic, hydrochloric, hydrobromic, sulfuric, benzenesulphonic, acetic, fumaric, dibenzoyl tartrate, malic and citric acids. The preferred salt is that of maleic acid.

The compounds of our invention, having formula I have been found to have bronchodilator activity. When tested in accordance with the procedure disclosed in O. H. Siegmund, et al., Journal of Pharmacological and Experimental Therapeutics 90, 254 (1949), the compound of Example 3, 1,2,3,4-tetrahydro-8,9-dimethoxy-3-[2-methyl-2-(1-piperidinyl)ethyl]-5H-[1]benzopyrano[3,4-c]-pyridin-5-one, differs significantly from 1,2,3,4-tetrahydro-8,9-dimethoxy-3-(2-piperidinylethyl)-5H-[1]-benzopyrano[3,4-c]pyridine-5-one which is disclosed in U.S. Pat. No. 3,964,008, and from 1,2,3,4-tetrahydro-8,9-dimethoxy-3-[1-methyl-2-(1-piperidinyl)ethyl]-5H-[1]benzopyrano[3,4-c]-pyridin-5-one which is disclosed in U.S. Pat. No. 4,013,671.

In the procedure described in the Journal of Pharmacological and Experimental Therapeutics, guinea pigs, when exposed to aerosols of methacholine, histamine, or serotonin, will collapse within about two minutes due to bronchoconstriction and apnea; pretreatment of the animals with bronchodilating agents will lengthen the time of exposure to the aerosol required to induce collapse. To compare the bronchodilating activity of these three compounds, i.e., the 2-methyl-2-(1-piperidinyl)ethyl, the 2-piperidinoethyl and the 1-methyl-2-(1-piperidinyl)ethyl substituted benzopyrano compounds, the amount of compound necessary to extend the period before collapse in pretreated animals to ten minutes was determined.

A dose of 3 mg/kg of body weight of the 2-piperidinoethyl compound of U.S. Pat. No. 3,946,008 was required to extend the period to ten minutes when the spasmogen was histamine while 100 mg/kg of body weight failed to extend the period to ten minutes when the spasmogen was the cholinergic agonist, methacholine. With 2-methyl-2-(1-piperidinyl)ethyl substituted compound (Example 3) a dose of 100 mg/kg failed to extend the time period to ten minutes when histamine was the spasmogen while a dose of 30 mg/kg of body weight extended the period to ten minutes when methacholine was the spasmogen. The 1-methyl-2-(1-piperidinyl)ethyl compound of U.S. Pat. No. 4,013,671 was inactive in both tests at comparable dosages.

These results indicate that the 2-methyl-2-(1-piperidinyl)ethyl compound of Example 3 possesses good anticholinergic activity, a type of activity believed to be essential for products to be effective bronchodialators in man (*Asthma* ed. K. Frank Austen and Lawrence M. Lichtenstein; J. A. Nadel, Neurophysiologic Aspects of Asthma and Warren M. Gold, Cholinergic Pharmacology in Asthma, Academic Press, N.Y., 1973), while the 2-piperidinoethyl compound of U.S. Pat. No. 3,946,008 and the 1-methyl-2-(1-piperidinyl)ethyl compound of U.S. Pat. No. 4,013,671 have for all practical purposes no anticholinergic activity.

In a further screening protocol anesthetized dogs were connected through tracheal and intrapleural cannulas to a Buxco pulmonary mechanics computer. The femoral vein was cannulated for infusion of pilocarpine, a well known cholinergic agonist.

The test compounds were given intravenously to measure their effect on the inhibition of the pilocarpine-induced bronchial constriction $ID_{50}$. The 2-piperidinoethyl substituted benzopyrano compound of U.S. Pat. No. 3,946,008 had an $ID_{50}$ in this test, of 3 mg/kg intravenously. In contrast thereto the compounds of the invention, i.e., the racemic 2-methyl-2-(1-piperidinyl)ethyl substituted compound (Example 3), had an $ID_{50}$ of 125 µg/kg; the corresponding levo isomer of Example 4 had an $ID_{50}$ of 31 µg/kg; the 2-methyl-2-(1-pyrrolidinyl)ethyl compound of Example 5 had an $ID_{50}$ of 17 µg/kg; and 1,2,3,4-tetrahydro-7,8-dimethoxy-3-[2-methyl-2-(1-piperidinyl)ethyl]-5H-[1]benzopyrano[3,4-c]pyridin-5-one had an $ID_{50}$ 97 µg/kg.

In summary, the compounds of the invention are orally effective anticholinergic bronchodilators selective for the bronchi. These compounds are useful in the treatment of asthma, bronchitis, emphysema and other diseases resulting in bronchoconstriction, especially those such as status asthmaticus, which by definition are resistant to sympathomimetic agents.

In another aspect of the invention there are provided pharmaceutical compositions comprising a compound of formula I as has been defined or a pharmaceutically acceptable acid addition salt thereof together with any of the conventional pharmaceutically acceptable carriers or excipients.

The compositions may be administered parenterally in combination with conventional injectable liquid carriers such as sterile pyrogen-free water, sterile peroxide-free ethyl oleate, dehydrated alcohol or propylene glycol. Conventional pharmaceutical adjuvants for injection solutions such as stabilizing agents, solubilizing agents and buffers, for example, ethanol, complex forming agents such as ethylene diamine tetraacetic acid, tartrate and citrate buffers and high-molecular weight polymers such as polyethylene oxide for viscosity regulation may be added. Such compositions may be injected intramuscularly, intraperitoneally, or intravenously.

The compositions are preferably formulated into orally administratable solid or liquid compositions or aerosols containing one or more physiologically compatible carriers or excipients. The oral compositions may, if desired, contain conventional ingredients such as binding agents, for example, syrups, acacia, gelatin, sorbitol, tragacanth, or polyvinylpyrollidone; fillers, for example, lactose, mannitol, starch, calcium, phosphate, sorbitol or methylcellulose; lubricants, for example, magnesium stearate, high-molecular weight polymers such as polyethylene glycols, high-molecular weight fatty acids such as stearic acid or silica; disintegrants, for example, starch; acceptable wetting agents as, for example, sodium lauryl sulfate. These compositions may take any convenient form, for example, tablets, capsules, lozenges, aqueous or oily suspensions, emulsions, or dry products suitable for reconstitution with water or other liquid medium before use. The liquid oral forms of administration may, or course, contain flavors; sweeteners; preservatives, for example, methyl or propyl p-hydroxybenzoates; suspending agents, for example, sorbitol, glucose or other sugar syrup, methyl, hydroxymethyl, or carboxymethyl celluloses, or gelatin; emulsifying agents as, for example, lecithin or sorbitan monooleate; or thickening agents. Non-aqueous compositions may also be formulated which comprise edible oils as, for example, fish-liver or vegetable oils. These liquid compositions may conveniently be encapsulated in, for example, gelatin capsules in a unit dosage amount.

A particular aspect of this invention comprises a compound of formula I in an effective unit dose form. By "effective unit dose" is meant a predetermined amount sufficient to be effective to bring about the desired bronchodilating effect.

In a further aspect of the invention there is provided a method of producing a bronchodilation in mammals, including man, which comprises the administration of an effective bronchodilating amount of a compound of formula I or a pharmaceutically acceptable acid addition salt thereof.

The dosage of the compounds of formula I or their pharmaceutically acceptable acid addition salts depends, of course, on the nature and severity of the biological reaction to be countered, as well as the path of administration. Usually the clinical dosage will be between 10 to 20 mg t.i.d. or q.i.d. for a 75 kg man. A 10 mg dose corresponds to 133 µg/kg of body weight.

The invention is illustrated by the following examples.

EXAMPLE 1

1,2,3,4-Tetrahydro-8,9-dimethoxy-5H-[1]benzopyrano[3,4-c]pyridin-5-one Hydrochloride A mixture of 46.0 g (0.3 m) of 3,4-dimethoxyphenol and 41.7 g (0.2 m) of 3-carbethoxy-4-piperidone HCl was cooled in an ice bath and treated with 100 cc of 73% v/v $H_2SO_4$ in ½ hr with stirring and protection from moisture. After stirring 4 days at room temperature the reaction was chilled and treated with an additional 24 g (0.156 m) of the phenol. After 5 days a second 24 g portion of the phenol was added. After stirring 6 days the reaction was treated with 150 g of ice and conc. $NH_4OH$ to pH 8-9. The resultant gum was stirred with 150 cc $CHCl_3$ for ½ hr and was filtered. The filtrate was evaporated and the resultant gum was triturated with pet ether followed by ethyl ether. The resultant solid was crystallized from 150 cc 3 N HCl affording 33.4 g of the pyridin-5-one as the hydrochloride, mp 254°-6° C.

Anal. Calcd. for $C_{14}H_{15}NO_4 \cdot HCl \cdot \frac{1}{2}H_2O$: C, 54.82; H, 5.59; N, 4.57; Cl, 11.56. Found: C, 54.73; H, 5.91; N, 4.38; Cl, 11.64.

EXAMPLE 2

1,2,3,4-Tetrahydro-8,9-dimethoxy-3-acetonyl-5H-[1]benzopyrano[3,4-c]pyridin-5-one A solution of 26.1 g (0.1 m) of 1,2,3,4-tetrahydro-8,9-dimethoxy-5H-[1]benzopyrano[3,4-c]pyridine-5-one, prepared in Example 1, 13 g (0.14 m) of chloroacetone, and 14.2 g (0.14 m) of triethylamine in 450 ml of ethanol was refluxed overnight. After evaporation, the residue was partitioned between dilute NaOH solution and $CHCl_3$. After drying ($Na_2SO_4$) and evaporation of the $CHCl_3$ extract, the residue was triturated with pet ether and 27.2 g of product filtered off. Crystallization from methanol afforded analytical material, mp 168°-72° C.

Anal. Calcd. for $C_{17}H_{19}NO_5$: C, 64.34; H, 6.04; N, 4.41. Found: C, 64.43; H, 6.08; N, 4.58.

EXAMPLE 3

1,2,3,4-Tetrahydro-8,9-dimethoxy-3-[2-methyl-2-(1-piperidinyl)-ethyl]-5H-[1]benzopyrano[3,4-c]pyridin-5-one and the Maleate Salt Thereof A solution of 3.17 g (0.01 m) of 1,2,3,4-tetrahydro-8,9-dimethoxy-3-acetonyl-5H-[1]benzopyrano[3,4-c]pyridin-5-one, prepared in Example 2, and 8.5 g (0.1 m) of piperidine in 50 ml of methanol was hydrogenated over 0.3 g 10% Pd/C at 100° C. and 360 lbs for 17 hrs. After filtration and evaporation, the residue was crystallized twice from isopropyl ether affording 1.1 g of analytical material, mp 105°-109° C.

Anal. Calcd. for $C_{22}H_{30}N_2O_4$: C, 68.37; H, 7.82; N, 7.25. Found: C, 68.08; H, 8.09; N, 7.11.

To a solution of 1100 g (2.85 m) 1,2,3,4-tetrahydro-8,9-dimethoxy-3-[2-methyl-2-(1-piperidinyl)ethyl]-5H-[1]benzopyrano[3,4-c]pyridin-5-one in 18.95 L ethyl acetate was added a solution of 345.6 g (2.97 m) maleic acid in 8.2 L ethyl acetate at 70° C. over a 30 minute period. Solid appeared when the addition was 45% complete. After the addition was complete the mixture was allowed to cool to room temperature with stirring for 2 hours. The solid was collected by filtration, washed with ethyl acetate and dried at 50° C. to yield 1290 g of 1,2,3,4-tetrahydro-8,9-dimethoxy-3-[2-methyl-2-(1-piperidinyl)ethyl]-5H-[1]benzopyrano[3,4-c]pyridin-5-one maleate as a yellow solid, mp 171°-175° C.

The product was recrystallized from 18 L of absolute ethanol. Two crops were obtained weighing a total of 1072 g. Non-aqueous titration indicated a purity of 101.5% and 100.7% respectively.

EXAMPLE 4

(−)1,2,3,4-Tetrahydro-8,9-dimethyoxy-3-[2-methyl-2-(1-piperidinyl)ethyl]-5H-[1]benzopyrano[3,4-c]pyridin-5-one (+)Dibenzoyl-D-tartaric acid monohydrate (182 g, 0.484 mole) and racemic 1,2,3,4-tetrahydro-8,9-dimethoxy-3-[2-methyl-2-(1-piperidinyl)ethyl]-5H-[1]-benzopyrano[3,4-c]pyridin-5-one, prepared in Example 3, were dissolved in 1.5 L of 95% ethanol with heat. The solution was allowed to stand overnight (18 hours) at room temperature. The yellow crystalline solid which formed was collected by filtration, washed with 95% ethanol (4×250 ml) and then with ether (2 L) to obtain 142 g (49.8%) of a cream colored solid, mp 138°-143° dec. The crude salt was recrystallized ten times from about 1 liter of 95% ethanol to obtain constant rotating product. The yield of the purified (+) dibenzoyl-D-tartrate salt of (−) 1,2,3,4-tetrahydro-8,9-dimethyoxy-3-[2-methyl-2-(1-piperidinyl)ethyl]-5H-[1]benzopyrano[3,4-c]-pyridin-5-one was 23.6 g; mp 176°-177° C. (dec.).

The free base was obtained by partitioning 9.0 g (11.8 mmol) of the above salt in a chloroform (250 ml) and 0.25 N NaOH (360 ml) mixture with stirring. The chloroform layer was separated, dried ($Na_2SO_4$) and the chloroform evaporated to obtain the free base as a yellow oil. Trituration of the oily residue with ether gave 4.1 g of the free base as a pale yellow powder, mp 109.5°-111.5° C. $[\alpha]_{589}^{23} = -5.55°$ (c, 2.70, methanol).

EXAMPLE 5

1,2,3,4-Tetrahydro-8,9-dimethoxy-3-[2-methyl-2-(1-pyrrolidinyl)ethyl]-5H-[1]benzopyrano[3,4-c]pyridin-5-one In a manner similar to Example 3, 6.34 g (0.02 m) of 1,2,3,4-tetrahydro-8,9-dimethoxy-3-acetonyl-5H-[1]benzopyrano[3,4-c]-pyridin-5-one and 14.2 g (0.2 m) of pyrrolidine afforded 7.0 g of crude material after trituration with petroleum ether. Crystallization from CH₃CN followed by recrystallization from methanol afforded analytical material, mp 139°–141° C.

Anal. Calcd. for $C_{21}H_{28}N_2O_4$: C, 67.72; H, 7.58; N, 7.52. Found: C, 67.72; H, 7.75; N, 7.46.

We claim:

1. A compound of the formula:

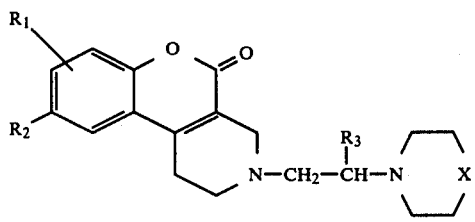

wherein $R_1$ and $R_2$ are lower alkoxy of 1–6 carbon atoms; $R_3$ is lower alkyl of 1–6 carbon atoms and X is $CH_2$ or a bond connecting the adjacent carbon atoms and the pharmaceutically acceptable acid addition salts thereof.

2. The compound of claim 1 wherein $R_1$ and $R_2$ are methoxy.

3. The compound of claim 2 which is 1,2,3,4-tetrahydro-8,9-dimethoxy-3-[2-methyl-2-(1-piperidinyl)ethyl]-5H-[1]benzopyrano-[3,4-c]pyridin-5-one and pharmaceutically acceptable acid addition salts thereof.

4. The compound of claim 3 which is 1,2,3,4-tetrahydro-8,9-dimethoxy-3-[2-methyl-2-(1-piperidinyl)ethyl]-5H-[1]-benzopyrano[3,4-c]pyridin-5-one maleate.

5. The compound of claim 2 which is 1,2,3,4-tetrahydro-8,9-dimethoxy-3-[2-methyl-2-(1-pyrrolidinyl)ethyl]-5H-[1]-benzopyrano[3,4-c]pyridin-5-one and pharmaceutically acceptable acid addition salts thereof.

6. The levo rotary optical isomer of the compound of claim 3, which is (−) 1,2,3,4-tetrahydro-8,9-dimethoxy-3-[2-methyl-2-(1-piperidinyl)ethyl]-5H-[1]benzopyrano-[3,4-c]pyridin-5-one and the pharmaceutically acceptable acid addition salts thereof.

7. A method for the treatment of bronchial constriction which comprises administration of an effective amount of a compound according to claim 1 to a mammalian host.

8. A pharmaceutical composition for bronchial dilation comprising a compound according to claim 1 in an amount sufficient to cause bronchodilation in a mammal in admixture with a liquid or solid pharmaceutically acceptable carrier material.

* * * * *